United States Patent
Mitteness et al.

(10) Patent No.: US 9,849,175 B2
(45) Date of Patent: *Dec. 26, 2017

(54) COMPOSITION AND METHOD FOR PREVENTING/DECREASING RESPIRATORY ILLNESS

(71) Applicant: Camas, Inc., Le Center, MN (US)

(72) Inventors: Bradley M Mitteness, Ghent, MN (US); Connie Phillips, St. Peter, MN (US)

(73) Assignee: CAMAS INCORPORATED, Le Center, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/785,838

(22) Filed: Mar. 5, 2013

(65) Prior Publication Data
US 2013/0183286 A1    Jul. 18, 2013

Related U.S. Application Data

(63) Continuation of application No. 13/103,559, filed on May 9, 2011, now abandoned, which is a continuation of application No. 10/775,557, filed on Feb. 10, 2004.

(60) Provisional application No. 61/332,421, filed on May 7, 2010, provisional application No. 60/447,904, filed on Feb. 19, 2003.

(51) Int. Cl.
*A61K 39/395* (2006.01)
*C07K 16/02* (2006.01)

(52) U.S. Cl.
CPC ............ *A61K 39/395* (2013.01); *C07K 16/02* (2013.01)

(58) Field of Classification Search
None
See application file for complete search history.

(56) References Cited

U.S. PATENT DOCUMENTS

| | | | |
|---|---|---|---|
| 4,166,867 A | 9/1979 | Betz et al. | |
| 4,550,019 A | 10/1985 | Polson | |
| 4,748,018 A * | 5/1988 | Stolle et al. | 424/157.1 |
| 4,748,019 A | 5/1988 | Lysons | |
| 5,080,895 A | 1/1992 | Tokoro | |
| 5,196,193 A | 3/1993 | Carroll | |
| 5,367,054 A | 11/1994 | Lee | |
| 5,420,253 A * | 5/1995 | Emery et al. | 530/423 |
| 5,443,976 A | 8/1995 | Carroll | |
| 5,556,744 A | 9/1996 | Weiner et al. | |
| 5,585,098 A | 12/1996 | Coleman | |
| 5,753,268 A | 5/1998 | Stolle et al. | |
| 6,068,862 A | 5/2000 | Ishihara et al. | |
| 6,086,878 A | 7/2000 | Adalsteinsson et al. | |
| 6,156,726 A * | 12/2000 | Newcomb et al. | 514/11.6 |
| 6,337,070 B1 | 1/2002 | Okuno et al. | |
| 7,256,270 B2 | 8/2007 | Nash et al. | |
| 2002/0012666 A1 * | 1/2002 | Greenblatt et al. | 424/183.1 |
| 2002/0098181 A1 | 7/2002 | Nash et al. | |
| 2002/0117552 A1 * | 8/2002 | Traylor | A23L 1/22 239/1 |
| 2004/0161427 A1 * | 8/2004 | Nash et al. | 424/164.1 |
| 2007/0218114 A1 * | 9/2007 | Duggan et al. | 424/443 |
| 2011/0033544 A1 * | 2/2011 | Nagata et al. | 424/489 |
| 2011/0166328 A1 * | 7/2011 | Nguyen | 530/387.1 |
| 2013/0183286 A1 * | 7/2013 | Mitteness et al. | 424/130.1 |

FOREIGN PATENT DOCUMENTS

| | | | |
|---|---|---|---|
| FR | 2 810 550 | * | 12/2001 |
| JP | 62-175426 | * | 1/1987 |
| WO | WO 2007068154 | * | 6/2007 |

OTHER PUBLICATIONS

Derwent ACC-No. 2007-675334 translation of WO 2007068154. Jun. 2007.*
Cuceanu et al. (Roum Arch Microbiol. Immunol. Jul.-Sep. 1991; 50 (3): 215-22, abstract only).*
Nierynck et al. (Nature Medicine. Oct. 1999; 5 (10): 1157-1163).*
Weltzin et al. (Clinical Microbiology Reviews. Jul. 1999; 12: (3): 383-393).*
Lee et al. (Journal of Pharmaceutical Sciences. Jun. 2000; 89 (7): 850-866).*
Beck et al. (Avian Diseases. 2003; 47: 1196-1199).*
USDA Agriculture Research Service Nutritional Nutrient Database for Standard Reference Release 27; Basic Report 01123, Egg, whole, raw, fresh. Feb. 26, 2015.*

(Continued)

*Primary Examiner* — Shanon A Foley
(74) *Attorney, Agent, or Firm* — Westman, Champlin & Koehler, P.A.; Z. Peter Sawicki; Visala Goswitz

(57) ABSTRACT

A microbial adherence inhibitor in the form of fowl egg antibodies is disclosed, along with the method of making it and methods of using it. The inhibitor functions by substantially preventing the attachment of adherence of colony-forming immunogens in the respiratory tracts of host animals and humans. The inhibitor is made by inoculating female birds with the immunogen, harvesting the eggs which contain antibodies to the immunogen, and separating the yolk and albumin from the shells of the eggs. The yolk and albumin contents are administered to animals or human by distributing the contents directly or introducing the contents entrained in air. The adherence inhibiting material can be formulated for use in a variety of ways such as an oral spray or a nasal spray. These formulations can be effective to prevent or reduce respiratory illnesses in animals and humans.

22 Claims, No Drawings

(56) References Cited

OTHER PUBLICATIONS

Ewert et al. (Infection and Immunity. Apr. 1979; 24 (1): 269-275).*
Espacenet English translation of Bruttmann et al. (FR 2 810 550); Dec. 2001.*
Pauly et al. "IgY technology: extraction of chicken antibodies from egg yolk by polyethylene glycol (PEG) precipitation." Journal of visualized experiments: JoVE 51 (2011).*
http://convert-to.com/725/quail-eggs-nutrition-details-units-conversion.html; pp. 3-6; accessed Jun. 23, 2016.*
Adachi et al. (Experimental and Therapeutic Medicine. 2011; 2: 41-45).*
Christopher-Henning et al., Porcine reproductive and respiratory syndrome (PRRS) diagnostics: Interpretation and limitations, Journal of Swine Health and Production, vol. 10, No. 4, pp. 213-218, 2002.
Corbeil et al., Bovine IgG2a Antibodies to Haemophilus somnus and allotype expression, Can. J. Vet. Res. vol. 61, pp. 207-213, 1997.
Faber et al., The costs and predictive factors of bovine respiratory disease in standardized steer tests; 1999 Beef Research Report, Iowa State University, 11 pages, A.S. Leaflet R1648, 1999.
Veterinary Services, Info Sheet: Treatment of respiratory disease in U.S. feedlots, Oct. 2001, 4 pages #N 347-1001, USDA-APHIS, 2001.
Jones et al., Protection of lambs against experimental pneumonic pasteurellosis by transfer of immune serum, Veterinary Microbiology, vol. 20, pp. 59-71, 1989.
Kirkwood et al., Effect of pig age and autogenous sow vaccination on nasal mucosal colonization of pigs by Haemophilus parasuis, Journal of Swine Health and Production, vol. 9, No. 2, pp. 77-79, 2001.
Krause et al., An rRNA approach for assessing the role of obligate amino acid-fermenting bacteria in ruminal amino acid deamination, Applied and Environmental Microbiology, vol. 62, No. 3, pp. 815-821, 1996.
Lin, Intraspecies differentiation of Mycoplasma hyopneumoniae field strains isolated in the United States, American Association of Swine Veterinarians, pp. 225-235, 2001.
Lu et al., A monoclonal antibody against a Pasteurella multocida outer membrane protein protects rabbits and mice against pasteurellosis, Infection and Immunity, vol. 50, No. 1, pp. 172-180, 1991.
Miniats et al., Vaccination of gnotobiotic primary specific pathogen-free pigs against Haemophilus parasuis, Can. J. Vet Res., vol. 55, pp. 33-36, 1991.
Ramos-Vara et al., Metritis, valvular endocarditis, and septicemia by actinobacillus equuli in a gilt in the United States, Vet. Pathol., vol. 45, pp. 495-499, 2008.
Regula et al., Comparison of serologic testing and slaughter evaluation for assessing the effects of subclinical infection on growth in pigs, JAVMA, vol. 217, No. 6, pp. 888-895, 2000.
Rimler, Passive immune cross-protection in mice produced by rabbit antisera against different serotypes of Pasteurella multocida, J. Comp. Path., vol. 114, pp. 347-360, 1996.
Showder et al., Bovine respiratory disease in feedlot cattle: environmental, genetic and economic factors, American Socity of Animal Science, Vo. 84, pp. 1999-2008, 2006.
Smith, Denetal caries vaccines: prospects and concerns, Critical Reviews in Oral Biology & Medicine, vol. 13, No. 4, pp. 335-349, 2002.
Smith et , Passive transfer of immunoglobulin Y antibody to *Streptococcus* mutans glucan binding protein B can confer protection against experimental dental caries, Infection and Immunity, vol. 69, No. 5, pp. 3135-3142, 2001.
Stovall et al., Impact of bovine respiratory disease during the receiving period on feedlot performance and carcass traits, Animal Science Peswich Report, pp. 82-86, 2000.
Part I: Reference of swine health and management in the United States, National Animal Health Monitoring System, Swine Survey 2000, USDA-APHIS, 62 pages, 2000.
Van Donkersgoed et al., Effects of various vaccination protocols on passive and active immunity to Pasteurella haemolytica and Haemophilus somnus in beef calves, Can. Vet. J., vol. 36, pp. 424-429, 1995.
Yokoyama et al., Passive protective effect of chicken egg yolk immunoglobulins against experimental enterotoxigenic *Escherichia coli* infection in neonatal piglets, Infection and immunity, vol. 60, No. 3, pp. 998-1007, 1992.
Otae et al., Transmission of PRRSO, Recnt research reports, Intronataral Piglettes, vol. 22, No. 7, 37, 2002, pp. 40-42.
Sheidt, "Mycoplasma pneumonia", Proceedgins of North Carolina Healthy Hogs Seminar, 1993, 2 pages.
Straw et al., "Mycoplasma pneumonia of swine", Cooperative Extension Service, 5 pages, Oct. 28, 2011.
Thacher et al., "Which bag is it? SIV or M. Hyo?", Focus on Swine Health & Performance, vol. 5, No. 3, 2001, pp. 1-4.
Lin, "A molecular approach to the differentials of atypical actinobacillus pleuropneumoniae field strains isolated in the United States", Am. Association Swine Vet., 2002, pp. 209-213.
Yaerger, "The impact of exposure dose on PRRSO induced reproductive disease in vaccinated and unvaccinated cows", Proceedings of Swine Disease Conference for Swine Practitioners, 1999, pp. 74-75.
Yokoyama et al., "Passive protective effect of chicken egg yolk immunoglobulins against experimental enterotoxigenic *E. coli* infection in neonatal piglets", Infect and Immun, vol. 60, No. 3, 1992, pp. 998-1007.
Hament et al., "Enhanced adherence of *Stretococcus* pneumoniae to human epithelial cells infected with respirator syncytial virus." Pediatric Research, vol. 55, No. 6, pp. 972-978, 2004.
Avadhanula et al., "Respiratory viruses augment the adhesion of bacterial pathogens to respiratory epithelium in a viral species and cell type-dependent manner." J. Virol., vol. 80, No. 4, pp. 1629-1636 (2006).
Chan et al., "Analytical sensitivity of rapid influenze antigen detection test for swine-origin influenze virus (H1N1)." Journal of Clinical Virology, vol. 45, pp. 205-207, 2009.
Hatta, H, Tsuda, K., Akachi., S. et. al. Oral passive immunization effect of anti-human rotavirus IgY and its behavior against proteolytic enzymes. 1993. Bioscience, biotechnology, and biochemistry. 57(7): 1077-1081.
Japanese Laid-Open No. S62-215534.
Japanese Unexamined Patent Application Publication No. 2001-515050.
Lin, C. B. A molecular approach to the differntials of atypical Actinobacillus pleuropneumoniae field strains isolated in the United States, Am. Association Swine Vet: 209-213, 2002.
Lu Y S; Lai W C; Pakes S P; Nie L C: "A monoclonal antibody against a Pasteurella multocida outer membrane protein protects rabbits and mice against pasteurellosis." Infection and Immunity, vol. 59, No. 1, Jan. 1991 (Jan. 1991), pp. 172-180, US.
Peralta, R.C., Yokoyama, H., Ikemori, Y., Et al. Passive immunisation against experimental salmonellosis in mice by orally administered hen egg-yolk antibodies specific for 14-kDa fimbriae of *Salmonella enteritidis*. 1994. J. Med. Microbiol. 41: 29-35.
Shin, N.R., Choi, I.S., Kim, J.M., et al. Effective methods for the production of immunoglobulin Y using immunogens of Bordetella bronchiseptica, Pasteurella multocida and Actinobacillus pleuropneumoniae. 2002. J. Vet. Sci. 3(1): 47-57.

* cited by examiner

COMPOSITION AND METHOD FOR PREVENTING/DECREASING RESPIRATORY ILLNESS

CROSS-REFERENCE TO RELATED APPLICATIONS

The present application is a continuation of and claims priority of U.S. patent application Ser. No. 13/103,559, filed May 9, 2011, which claims the benefit of U.S. provisional patent application Ser. No. 61/332,421; and is a continuation in part of and claims priority of U.S. patent application Ser. No. 10/775,557, filed Feb. 10, 2004, which claims the benefit of U.S. provisional patent application Ser. No. 60/447,904, filed Feb. 19, 2003, the contents of all of the above are hereby incorporated by reference in their entirety.

FIELD OF THE INVENTION

This invention is directed to microbial adherence inhibitors, in the form of fowl egg antibodies, for substantially preventing the attachment or adherence of colony-forming illness-causing immunogens in respiratory disease complex by inhibiting the immunogen's ability to adhere to the mucous membranes of animals including host food animals, high value nonfood animals, zoological animals, companion animals, laboratory animals or humans, to the method of producing such adherence inhibitors, and to the methods of using such inhibitors.

BACKGROUND OF THE INVENTION

A group of microorganisms form a very complex interaction in the respiratory tract of animals. These animals can be dairy cattle, feedlot cattle, swine, and birds such as chickens and turkeys to name a few. Although the organisms can vary from animal group to animal group, they are basically bacteria such as *Pasteurellae, Mannhiemae,* and *Haemophilus* groups, *Mycoplasma*, and viruses of the respiratory groups such as bovine respiratory syncytial virus (BRSV), bovine viral diarrhea (BVD), parainfluenza (PI$_3$), infectious bovine rhinotracheitis (IBR), swine influenza, (H$_1$N$_1$, H$_3$N$_2$), fungi and parasites and combinations of the same. These organisms are considered as opportunistic respiratory pathogens that may reside in the upper respiratory tract of healthy animals. *Pasteurella* and to a lesser extent *Haemophilus* and *Mycoplasma* species may cause bovine respiratory disease complex (BRDC) in cattle by the result of invasion of the lower respiratory tract after infections of the nasopharynx. In dairy or feedlot cattle, a variety of stressful situations such as shipment, weaning, viral infections, bad weather, change in weather, movement in feedlots, poor nutrition, and overcrowding can impair the competence of the immune system and the physical and immunological defenses of the animals. This allows greater numbers of microorganisms to make the journey from the nasopaharyngeal area to the lower respiratory tract to the interior of the lungs. This leads to the pneumonic respiratory disease complex, which includes the shipping fever complex in cattle. Transmission between animals is usually by airborne droplets or by food or water contamination. Once the microorganisms are established in the nasopharyngeal area, during inspiration the aerosols can result in downward carriage of the bacterial or viral pathogens into the lower respiratory tract. This allows the organisms to attach to the bronchi and alveolar cells and to multiply causing pneumonia. Respiratory infections can lead to lesions with no clinical signs but lead to lower average daily gain. Animals can go off feed, become very ill rapidly and death can occur within hours. Morbidity can be very high and once one animal becomes ill the rest of the herd are easier to infect. This becomes a major concern for feedlots. Similar outbreaks occur in swine herds and flocks of birds such as chickens and turkeys. Current live vaccines have had limited success in protecting the animals against this complex. This may in part be due to the lack of immune protection in the nasopharyngal area. The group of respiratory viruses can weaken the animals and decrease the immunological response of the host, it is the bacterial strains (usually *Mannhiema hemolytica* or *Pasteurella multocida*) that invade the lower respiratory tract leading to bronchopneumonia (BRD) that lead to disease and death of the animal. By blocking the viral infection, bacterial infections should be reduced. In both shipping fever pneumonia and enzootic pneumonia in cattle, the final common denominator in both types of disease are the bacterial agents. Bovine respiratory disease (BRD) is the leading cause of disease related loss in feedlots today. Financial losses attributed to BRD include mortality, medication, veterinary, and labor costs for treatment. Average costs for one treatment average $8.80 per head. Heifers treated for BRD have lower morbidity scores by 37.9%. Animals that are never treated average $11.48 per head higher in net return. The average daily gains differ between treated and untreated animals. The net profit averages $57.48 lower per head for treated animals. BRD has been listed as causing 20.6% of all steer deaths in feedlots.

Porcine respiratory disease complex is a major and similar type of disease affecting up to 90% of all swineherds. *Mycoplasma hyopneumonia* is the primary pathogen commonly associated with the complex secondary pathogens such as *Pasteurella multocida* types A and D and can cause clinical signs of high fever or impaired growth. Combinations of these organisms can lead to both increase in severity and duration of pneumonia in swine. Porcine reproduction and respiratory syndrome (PRRS) can be another major cause of pneumonia in swine. This can lead to severe reproduction disease with only minimal dose of virulent PRRS stains. Common causation agents of Swine respiratory disease can include PRRS virus, swine influenza (H1N1, H3N2) and *Mycoplasma hyopneumoniae* along with *Haemophilus parasuis, Haemophilus suis, Haemophilus planopneumonia, Pasteurella (Mannhiema) haemolytica* and *Pasteurella multocida* (types A & D). Estimating the total economic impact on the health of these animals is difficult. Pneumonic lung lesions may cause poor respiratory health in herds and may affect up to 70 percent of the pigs in a herd. Combinations of vaccinations for viruses and medication for bacteria are needed to help control these problems-timing of vaccination is always important. Medication must be applied at the proper time to minimize costs and damage to the animals.

Organisms such as *Mycoplasma hyopneumoniae* can be a cause of an important chronic respiratory disease called "swine enzootic pneumonia" (SEP). This organism alone can produce severe pneumonia in swine and remains a significant threat to the swine industry.

*Actinobacillus pleuropneumoniae* causes "porcine pleuropneumoniae", resulting in serious financial losses and death. Although vaccines have been developed, homologous protection has not been demonstrated. During the past years, 14 serotypes and 2 biotypes have been identified worldwide. Both growing and finishing pigs must be vaccinated to protect herds.

The primary effect of respiratory disease in swineherds is seen in reduced feed intake that leads to impaired growth. This leads to less uniformity in pigs, more mortality, less average daily gain, and less pigs per litter. Producers report that almost 14.4% of all herd placements develop respiratory disease. Costs increase for injecting vaccines and medication, and lower overall performance. Estimates have been made that reduced daily weight gain and antibiotics used to treat disease cost the Swine industry 467 million dollars annually. Over 39% of all deaths in grower-finisher pigs had been attributed to respiratory diseases in swine.

PRIOR ART

The production of avian egg antibody for the diagnosis or treatment of specific conditions has been known. The production of avian egg antibody for the inhibition of organisms, specifically the colonization of organisms, and the adherence and colonization of illness-causing immunogens in the respiratory tracts of animals is not suggested.

Representative prior art patents include the following:
Poison, U.S. Pat. No. 4,550,019
Stolle et al, U.S. Pat. No. 4,748,019
Tokoro, U.S. Pat. No. 5,080,895
Carroll, U.S. Pat. No. 5,196,193
Lee, U.S. Pat. No. 5,367,054
Coleman, U.S. Pat. No. 5,585,098
Stolle et al, U.S. Pat. No. 5,753,268

Poison, U.S. Pat. No. 4,550,019, is directed to the manufacture and use of fowl egg yolk antibodies for making immunological preparations for the passive immunizations of animals, including humans, as immuno reagents for immunosorbitive processes and in particular for quantitative analytical tests, especially micro assays for diagnostic, pathological, forensic, and pharmacokinectic investigations.

Stolle et al, U.S. Pat. No. 4,748,018, is directed to a method of passive immunization of mammals using avian egg yolk antibody against any of a variety of antigens using various methods of administration under various conditions and using various compositions incorporating the antibody, after first developing in the mammal a tolerance for the antibody.

Tokoro, U.S. Pat. No. 5,080,895, is directed to a specific antibody containing substance from eggs and method of production and use thereof for the treatment of infectious or other diseases, and as additives in food for livestock and poultry, cosmetics, and medicines, and in the field of serodiagnosis. Although not explicitly stated, it is apparent that the use of the egg antibody in feeds is to provide an easy means of oral administration of the antibody for the treatment of intestinal infections in livestock or poultry.

U.S. Pat. No. 5,196,193, and divisional U.S. Pat. No. 5,443,976, are directed to anti-venom compositions containing horse antibody or avian egg yolk antibody for neutralizing snake, spider, scorpion or jelly fish venom.

Lee, U.S. Pat. No. 5,367,054, is directed to methods for large scale purification of egg immunoglobulins to lower somatic cell count in the milk of lactating ruminants.

Stolle et al, U.S. Pat. No. 5,753,268, is directed to an anti-cholesterolemic egg vaccine and method for production and use as a dietary supplement for the treatment of vascular disorders in humans and other animals.

SUMMARY OF THE INVENTION

Broadly stated, this invention is directed to a method for the production of a microbial adherence inhibitor for administration to animals, such as host food animals, high value nonfood animals, zoological animals, companion animals, or humans to inhibit or substantially prevent the adherence of colony-forming immunogens and/or disease causing viruses in the respiratory tracts. The microbial adherence inhibitor can be generated by first inoculating female birds, in or about to reach their egg laying age, with the particular target immunogen. Then, after a period of time sufficient to permit the production in the bird of antibody to the targeted immunogen, the eggs laid by the birds are harvested. The yolk and albumin antibody-containing contents of the eggs are separated from the shells. The antibody-containing contents of the eggs may be used directly, placed on an extender, or mixed with carrier material. The antibody can be incorporated into a liquid, mixed into a lick tub, sprayed or squirted into the environment containing the animals. The antibody may also be incorporated into a nasal or an oral spray that can be administered into nasopharyngeal airways or orally. The antibody may also be incorporated onto strips that when placed in the mouth dissolve to release the antibodies into the mouth. The egg antibody adherence inhibiting material maybe stored or shipped for use as needed.

The egg contents incorporating the antibody specific to the targeted immunogens are administered to the animals or humans by distributing the antibody material directly or introducing antibody material entrained in air. The material can be introduced into the nasal pharyngeal area of the animal by intranasal application. Aerosol mixtures can be made and administered as a mist over the heads and nostrils of the animals. Another alternative is to mix the material with a carrier and administer as "top dressing" on feed. Special needs can be met by adding the material to water and letting the animals or humans drink the solution. The active material can be added to bulk licks or feed baskets for delivery. Gel-like mixtures can be made using common animal feed mixtures and poured into "lick tubs" (feed additive bulk tubs). Other delivery systems can be adapted for delivery of the active material to the respiratory tract.

In one aspect, the present invention relates to a composition for preventing or decreasing respiratory illness. The composition includes adherence inhibiting material produced in eggs laid by female birds, wherein the birds are inoculated with one or more viruses or viral antigens causing the respiratory illness. The adherence inhibiting material is formulated for dispersion into the respiratory tract to prevent or reduce the adherence of the virus causing the respiratory illness to the mucosal membranes of the respiratory tract.

In another aspect, the present invention relates to a method of preventing or reducing the incidence of respiratory illness caused by viruses in an animal. The method includes dispersing a composition comprising adherence inhibiting material produced in eggs laid by female birds, wherein the birds are inoculated with one or more viruses or virus antigens causing the respiratory illness, the composition formulated for dispersion into the respiratory tract to prevent or reduce the adherence of the virus causing the respiratory illness to the mucosal membranes of the respiratory tract.

Adherence inhibition as referred to herein relates to inhibition of adherence of microbes that prevents or reduces colony and/or plaque formation in the respiratory tract. In some embodiments, adherence inhibitors prevent or reduce the ability of microbes such as bacteria to adhere to mucosal membranes and form colonies. In other embodiments, adherence inhibitors prevent or reduce the ability of microbes such as viruses to attach and enter cells, thus preventing or reducing the formation of additional viral particles.

DETAILED DESCRIPTION OF ILLUSTRATIVE EMBODIMENTS

The present invention is predicated on a method of inhibiting the ability of colony forming microorganisms, such as *Pasteurella* (*Mannhiema*) *haemolytica*, *P. multocida*, and *Haemophilus somnus*, Swine influenza, *Mycoplasma bovis* or *M. hyopneumoniae* from adhering to the mucous membranes and bronchi and alveolar cells of the respiratory tracts of animals thereby preventing colonization of the microorganisms. The failure of the microorganisms to colonize maintains the immunological defenses of the animals when subjected to stress inducing environments. The result is that the animals have less pneumonic respiratory diseases including shipping fever which cause high mortality of infected animals.

In some embodiments, the present invention can be used to inhibit respiratory disease causing viruses, particularly influenza viruses, in humans and animals. The disease causing viruses can be, for example, infectious Bovine Rhinotracheitis, (Herpesviridae); Bovine adenovirus 1-7, (Adenoviridae); Bovine Respiratory Coronavirus (Coronaviridae); Bovine Respiratory Syncytial Virus (Paramyxoviridae); Bovine Parainfluenza 3 (Paramyxoviridae).

All mammals and birds provide similar types of protection which allow for an immediate immune response in their very young offspring until they too acquire the ability to make the antibodies for themselves. More specifically called passive antibody protection, this defense mechanism is passed to the young of mammals through the placenta, the mother's milk, or through both. The young of birds, however, receive their passive antibody protection through the store of antibodies placed in the eggs in which they develop from the embryonic stage. Birds, in particular, have the ability to "load up" their eggs as they are formed, with a very large supply of antibodies concentrated over that which is present in the serum of the mother. In addition, avian antibodies are much more stable and resistant to inactivation through digestion than mammalian antibodies, especially under adverse conditions. Once immunized, the hen deposits IgY type immunoglobulins in the yolk while depositing IgM and IgA immunoglobulins in the albumin. The albumin helps add stability to the whole egg preparations and helps protect the avian antibodies. The avian IgY immunoglobulins in the yolk tightly bind to, coat, cover and obliterate adherins that attach themselves to their hosts. The IgM and IgA immunoglobulins in the albumin increase binding of the antibody containing material in the mucous tissue of the respiratory tract. This can provide longer sustaining effect of the antibody containing material. The larger antibody containing molecules are more effective in preventing adherence of the targeted immunogen in the respiratory tract of the animal or human. Albumin is a protein that protects the activity of the IgY immunoglobulins thereby increasing their active life in the respiratory tract. Furthermore, a large fraction of the antibodies deposited in the eggs by the hen are against the most recent antigenic challenges to the hen. This all results in the eggs of birds being a most ideal source for large quantities of economically produced highly specific and stable antibodies. While the invention is illustrated by the use of chickens to produce avian antibody, other fowl including turkeys, ducks, geese, ostrich, Emu, pheasant, pigeon, quail, etc. or combination thereof, may be used.

Specifically, groups are obtained of young hen chickens, typically Rhode Island Reds, White Leghorns, sex-linked hybrid crosses or other breeds suited to large egg size, high volume egg production and ease of handling which are about to reach laying age, about 16-19 weeks for chickens, on a schedule predetermined by the amount and timing of final product desired resulting in a steady continuous production stream. After a suitable period of isolation and acclimatization of about two to four weeks, each group will enter into an inoculation program using proprietary preparations of specific antigens (immunogens) to which an antibody is desired. The cultures of microorganisms may be obtained from commercial sources such as the American Type Culture Collection (ATCC) or from wild type isolates. The cultures may be used to isolate antigens. The antigens can be prepared as prepared immunogens and may be injected intramuscularly, but preferably injected subcutaneously. In approximately four to five weeks, the average egg collected will contain copious amounts of the desired specific antibody in a readily usable and stable form. The chickens may be reinoculated with the targeted immunogen throughout the egg laying period to maintain the high antibody level.

Batches of eggs from predetermined groups of chickens are cracked, the contents are separated from the shells and mixed and preferably pasteurized to eliminate potential pathogenic microorganism. Standard test procedures are used, such as ELISA, agglutination, or the like are used to the monitor the antibody activity. The typical batch is then blended with batches from groups of chickens at other average production levels resulting in abundant standardized active ingredients. The egg antibody microbial inhibitor material may be stored and shipped on carrier materials such as soy bean oil, boluses and/or tablets. Dependent on the needs and specifications of the formulator and the final customer, the final antibody products may include some type of innocuous additive, such as dried whey or soy hulls, distillers grains, molasses, soy or rice husks or the like for formulation with feed ration. The antibodies may also be purified, dried and lyophilized for storage for later use. This method provides for the first time, an economical, safe and effective means for controlling respiratory illness causing organisms in beef cattle and dairy herds, swine, chickens, turkeys, companion animals, high value nonfood animals, zoological animals and humans.

Immunogen adherence inhibitor and method of making and using same produces specific immunogens to the microbial species listed. The immunogens are used to immunize egg laying avian animals. The immunized hen will lay eggs containing the specific antibodies of the IgM and IgA type in the albumen and IgY type in the yolk. The eggs will be collected and material from the whole cracked egg will be mixed in the proper concentration with a carrier mixture such as molasses, soy oil, DMSO, PBS buffer and Vitamin E solution. This solution is optimized so it can be sprayed, squirted, injected intra-nasally, gelled, or as a top dressing on feed and in lick tubs. The protective material may be sprayed over the animals in the pens or feedlots during the feeding period usually once in the morning and once in the evening. The number of sprayings is determined from testing. Since the material is non-toxic, it is given as needed and as much as needed for a given pen. The preferred method is by direct intra-nasal injection with a spray using ½ dose per nostril or a combination of direct nasal spray plus top feed, lick tub, squirt applicators.

The product is an all natural preparation that contains specific avian antibodies to the targeted immunogens. These antibodies when attached to the outer surface cell wall, adherin receptors, pilii or pilated structures and capsule, or viral capsid will not allow the organism to attach to the mucous membranes. The microorganisms will not be able to multiply or colonize. It will keep the microorganisms from moving down the respiratory tract and eliminates the ability to cause disease in the lower respiratory tract. By spraying the material, the mist will coat the nasopharynx and prevent the bacteria, viruses or other microorganisms from being spread in water droplets. The mist will also coat the feed and water in the area, again blocking the ability of the pathogen of the organisms to spread from animal to animal. The method of the invention provides for a substantial decrease in animal illness and death in feedlots and pens without the use of antibiotics.

By reducing respiratory organisms, one will decrease lung lesions, reduce secondary infection, improve daily gain, improve performance, improve feed efficiency, and reduce costs. Controlling pneumonia in animals will improve growth performance and quality of life as well as lower potential spread of respiratory organisms. Similar examples can be obtained in companion animals or humans. It is apparent that many modifications and variations of this invention as hereinbefore set forth may be made without departing from the spirit and scope thereof. The specific embodiments described are given by way of example only and the invention is limited only by the terms of the appended claims.

The most successful colonizing microorganisms, bacteria, viruses and parasites, etc., have evolved a number of different types of molecules, referred to as "adherins" or "intimins", on their surfaces which can very tightly stick to one or more types of specific molecules that are part of the host's various surfaces. The adhesion inhibitor is an avian antibody of extraordinary high specific activity which can very tightly bind to, coat, cover and obliterate these adherins which attach themselves to their hosts with a lock and key type of fit to very unique chemical structures. The avian IgY immunoglobulins in the yolk tightly bind to, coat, cover and obliterate adherins which attach themselves to their hosts. The albumin, IgM and IgA immunoglobulins increase binding in the mucous tissue of the respiratory tract of the antibody containing material which provides longer sustaining effect of the antibody containing material. The larger antibody containing molecules are more effective in preventing adherence of the targeted immunogen in the respiratory tract of the animal or human. Albumin is a protein that protects the activity of the IgY immunoglobulins thereby increasing their active life in the respiratory tract. In addition to this direct attack, components of the complement system included in most biological fluids, such as blood, lymph, saliva, tears and to some extent intestinal secretions, recognize an antibody attachment as triggers for their many types of defensive activities. Specific antibody attachment and coating combined with the very likely mobilization of many other cellular defense systems, therefore, quickly culminating in the chemical inactivation and ultimately the destruction of the targeted microorganism.

In some embodiments, the immunogen adherence inhibitor may be directed towards antigens of influenza viruses and other microorganisms that may cause respiratory diseases in animals and/or humans. The viruses can be, for example, Orthomyxoviridae, specifically influenza, $H_1N_1$, $H_5N_1$, $H_3N_2$, or combinations thereof or other types of Hemagglutinin (H) and neuraminidase (N) combinations that are typically identified by an H number and an N number and their mutated strains; the Herpesviridae, specifically, Infectious Bovine Rhinotracheitis, 1 and 5; the Paramyxoviridae, specifically BRSV and $PI_3$; the Arteriviridae, specifically, porcine respiratory and reproductive syndrome virus (PRRSv) and the Adenoviridae, specifically Bovine adenovirus 1, 3, 5, 6, 7. The immunogen adherence inhibitor can include egg-derived antibodies along with a pharmaceutically appropriate carrier and a mucosal bioadhesive.

The immunogen adherence inhibitor can be delivered several times a day as a nasal spray depending on expected exposure to provide longer term or more intense protection. During influenza season, for example, applicators containing the immunogen adherence inhibitor can be carried by individuals expecting to be exposed to virus. Individuals flying on airplanes especially long airplane flights, for example, may carry the nasal spray and administer the spray multiple times during a flight to decrease the chance of infection from a virus or viruses. Individuals could easily apply specific antibodies, immunogen adherence inhibitors, to their upper airways prior to expected exposure by the method of a simple nasal spray. These antibodies would serve as a mucosal protectant to prevent the adherence, colonization and replication of the targeted virus or other microorganism in the human or animal host.

The nasal spray may deliver the pharmaceutical composition containing the immunogen adherence inhibitor in a variety of droplet sizes. The droplet size of the particular pharmaceutical composition in the nasal spray may be determined by the location in the respiratory tract that the target microorganism is expected to colonize. For example, the influenza virus, H5N1, generally colonizes deeper in the respiratory tract than the more typical seasonal H3N2 influenza virus. Thus, in preferred embodiments, an immunogen adherence inhibitor directed towards H5N1 may be delivered in a smaller droplet size to ensure delivery of the protection deeper in the respiratory tract.

Alternative methods for delivering the immunogen adherence inhibitor can also include a mouth rinse or a gargle. Impregnated strips with the immunogen adherence inhibitor designed to dissolve in the mouth to release antibodies can be used to coat the upper airways with the composition containing the immunogen adherence inhibitor.

The immunogen adherence inhibitor against an influenza virus may be prepared on a yearly or other periodic time frame before the influenza season. The immunogen adherence inhibitor administered may be based on the circulating strains of the viruses. As circulating strains change or the threat of a new, pandemic virus appears, the product may be updated simply by immunizing new chickens with the newest strain of interest. The birds may begin to deposit antibodies into their eggs specific to the newest strain or strains in as little as two weeks after immunization. In contrast, the prior art methods require a much longer time frame to produce, test and obtain regulatory approval for a new vaccine.

The invention is further illustrated by the following examples:

EXAMPLE 1

Selection of Egg Laying Avian Hens

The strain of egg laying hen may vary with needs and uses. Any egg laying fowl hens may be immunized including chickens, turkeys, ducks, goose, pigeon, quail, ostrich, emus or any other fowl. The common strains of egg laying chickens were preferred and are usually selected for the number of eggs laid per year, size of egg and ease of housing. Rhode Island Red, White Leghorn, and Red Sex Linked hybrids are the animals of choice based on egg size (large to ex-large, 50-65 gm) and were used for the immunization schedules. The ease of handling the animals and the size and uniformity of the eggs along with the number of eggs laid per hen per year were observed. Although any avian egg laying hen could be used, for cost and ease of use these chickens proved to work the best. The White Leghorn, W98 Hybrid gave the most uniformity and greater number of eggs per animal. These animals produce a large to extra-large grade of egg (50-65 gm) and up to 300 eggs a year per hen.

EXAMPLE 2

Preparation of PM Antigen for Immunogen

Pasteurella Multicoda (ATCC 15743) was used as a model bacteria. The organism was isolated from cattle. The ATCC method for rehydration of the stock was followed. The bacteria are re-hydrated in 1.0 ml of TSB. Brain Heart Infusion (BHI, Acumedia) is used to stimulate the PM antigens on the bacterium. Stock TSB is inoculated into BHI Broth and incubated at 37° C. for 18-24 hours. This stimulates somatic and attachment antigens development on the bacteria. Flasks containing BHI Broth are inoculated with the BHI Broth culture. While stirring slowly, flasks are incubated at 37° C. Blood agar plates are streaked for isolation of colonies to confirm the morphology. Good growth is seen after 22 hours. Flasks were combined and the material was harvested using centrifugation and sterile saline (0.9%) at approximately 3000 rpm for 30 minutes. The harvest was collected in tubes. Density was checked using spectrophotometer enumeration and McFarland nephelometer standards. The material was diluted to approximately $1 \times 10^9$ per ml. Four percent (4%) sodium deoxycholate (Difco) solution was added as a 1:1 ratio with culture in 0.9% sterile saline (Herzberg, 1972) and stirred for approximately 18 hours at room temperature (22° to 24° C.). The material was centrifuged to remove whole cells. Supernatant was used as stock for PM antigen. Dry weight was determined at approximately 14.9 mg/ml. The product is diluted in sterile PBS, pH 7.4 to 1 mg/ml for PM Immunogen.

EXAMPLE 3

Preparation of PH Antigen for Immunogen

Stock *P. Haemolytica* (ATCC 14000) was used for PH antigen. The organism was isolated from cattle. The ATCC method for rehydration of the stock was followed. The bacteria were re-hydrated in 1.0 ml of TSB. Brain Heart Infusion (BHI, Acumedia) and used to stimulate the PM antigens on the bacterium. Stock TSB was inoculated into BHI Broth and incubated at 37° C. for 18-24 hours. This stimulates somatic and attachment antigen development on the bacteria. Flasks containing BHI Broth were inoculated with the BHI Broth culture. The flasks were incubated at 37° C. while stirring slowly. Good growth was seen after 22 hours. Blood agar plates were streaked for isolation of colonies to confirm the morphology. Flasks were combined and the material was harvested using centrifugation and sterile saline (0.9%) at approximately 3000 rpm for 30 minutes. The harvest was collected in tubes. Density was checked using spectrophotometer enumeration and McFarland nephelometer standards. The material was diluted to approximately $1 \times 10^9$ per ml. Four percent (4%) sodium deoxycholate (Difco) solution was added as a 1:1 ratio with culture in 0.9% sterile saline (Herzberg, 1972) and stirred for approximately 18 hours at room temperature (22° to 24° C.). The material was centrifuged to remove whole cells. Supernatant was used as stock for PH antigen. Dry weight was determined. The product was diluted in sterile PBS, pH 7.4 to 1 mg/ml for PH Immunogen.

EXAMPLE 4

Preparation of HS Antigen for Immunogen

Stock *Haemophilus sommus* (ATCC 43626) was used as stock bacterial culture for HS antigen. The organism was isolated from cattle. The ATCC method for rehydration of the stock was followed. The bacteria were re-hydrated in 1.0 ml of TSB. ATCC medium: 814 GC Medium was used to stimulate the HS antigens on the bacterium. Stock TSB was inoculated into 814 GC Medium and incubated at 37° C. and 5% $CO_2$ for 18-24 hours. This stimulates somatic and attachment antigen development on the bacteria. Good growth was seen after 22-48 hours. Blood agar plates were streaked for isolation of colonies to confirm the morphology. Flasks were combined and the material is harvested using centrifugation and sterile saline (0.9%) at approximately 3000 rpm for 30 minutes. The harvest was collected in tubes. Density was checked using spectrophotometer enumeration and McFarland nephelometer standards. The material was diluted to approximately $1 \times 10^9$ per ml. Four percent (4%) sodium deoxycholate (Difco) solution is added as a 1:1 ratio with culture in 0.9% sterile saline (Herzberg, 1972) and stirred for approximately 18 hours at room temperature (22° to 24° C.). The material was centrifuged to remove whole cells. Supernatant was used as stock for HS antigen. Dry weight was determined. The product was diluted in sterile PBS, pH 7.4 to 1 mg/ml for HS Immunogen.

EXAMPLE 5

Preparation of HSa Antigen for Immunogen

Stock *Haemophilus suis* (ATCC 19417, *H. parasuis*) was used as stock for HSa antigen. The organism was isolated from swine. The ATCC method for rehydration of the stock was followed. The bacteria were re-hydrated in 1.0 ml of TSB. ATCC Medium 5129: *Haemophilus* Test Medium was used to stimulate the HSa antigens on the bacterium. Stock TSB was inoculated into #5129 Broth and incubated at 37° C. for 24-48 hours. This stimulated somatic and attachment antigen development on the bacteria. Flasks containing #5129 Broth or plates containing #814 Medium were inoculated with Stock Broth culture. Flasks were incubated at 37° C. and 5% $CO_2$. Good growth was seen after 48 hours. Blood agar plates were streaked for isolation of colonies to confirm the morphology. Flasks are combined and the material is harvested using centrifugation and sterile saline (0.9%) at approximately 3000 rpm for 30 minutes. The harvest was collected in tubes. Density was checked using spectrophotometer enumeration and McFarland nephelometer standards. The material was diluted to approximately $1 \times 10^9$ per ml. Four percent (4%) sodium deoxycholate (Difco) solution was added as a 1:1 ratio with culture in 0.9% sterile saline (Herzberg, 1972) and stirred for approximately 18 hours at room temperature (22° to 24° C.). The material was centrifuged to remove whole cells. Supernatant was used as stock for HSa antigen. Dry weight was determined The product was diluted in sterile PBS, pH 7.4 to 1 mg/ml for HSa Immunogen.

EXAMPLE 6

Preparation of ELISA Plates using PH, PM, HS and HSa Antigens for Monitoring Antibodies in Eggs Chickens and Feed PH, PM, HS and HSa ELISA: Ninety-six well assay plate (flat bottom Costar) were coated using 100 μg/ml with various concentration of antigens (10 μg-200 μg/ml) in carbonate buffer, ph 9.6. Plates were incubated between 22.degree. to 37.degree. C. for up to 18 hours. The wells were aspirated to prevent cross-contamination. The plates were blocked with 390 μl/well of 0.5% BSA and incubated at 37° C. for 1 hour. Plates were coated using alternative rows of positive or negative for controls. Plates were rinsed one time with wash buffer containing Tween™. 20. One hundred microliters per well of diluted sample were added to wells in duplicate wells, and incubated at 37° C. for one hour. Goat anti-chicken IgG conjugate with Horseradish peroxidase (Kirkegard and Perry Laboratories; 1:1000 to 1:3000) was added. After one hour incubation, the substrate (TMB, KPL) was added according to manufacturer's instructions and the reaction was stopped after 10 minutes with 0.1 M phosphoric acid. Optical densities of the wells were determined in Dynatech ELISA Reader at 450 nm and the information was recorded for further data analysis.

EXAMPLE 7

Analysis of Individual Eggs and Serum Over Time

Eggs were selected at various periods in the immunization period for monitoring antibody responses to the specific antigens. Selected chickens were monitored at day 0 and continued on a monthly basis after the fourth month. The whole egg was collected from the shell and then a 1 ml sample was taken. This sample was then extracted with buffer to analyze the antibody content. The standard ELISA's for the PH, PM, HS and HSa immunogens were used for analysis. The negative readings were subtracted from the OD readings.

EXAMPLE 8

Immunization of Chicken with PH Immunogen

Selected egg laying hens, White Leghorn, approximately 19 weeks old were injected with the stock PH immunogen. Four injections (500 μg, 100 μg, 200 μg, and 250 μg) were given one week apart. A serum sample was collected two weeks after the last initial injection. If boosters were needed, 100 μg was given in each booster (every six months). Within four weeks, all hens produced excellent antibodies in the eggs. ELISA PH readings averaged 1.00 OD for 1:300 dilution and 0.265 OD for 1:1,200.

EXAMPLE 9

Immunization of Chicken with PM Immunogen

Selected egg laying hens, White Leghorns, approximately 19 weeks old were injected with the stock PM Immunogen. Four injections (500 μg, 100 μg, 200 μg and 250 μg) were given one week apart. A serum sample was collected two weeks after the last initial injection. If boosters were needed, 100 μg was given in each booster (every six months). Within four weeks, all of the hens produced excellent antibodies in the eggs. ELISA PM readings averaged 1.42 OD for 1:300 dilution an 0.68 OD for 1:1,200.

EXAMPLE 10

Immunization of Chicken with HS Immunogen

Selected egg laying hens, White Leghorns, approximately 19 weeks old were injected with the stock HS Immunogen. Four injections (500 μg, 100 μg, 200 μg and 250 μg) were given one week apart. A serum sample was collected two weeks after the last initial injection. If boosters were needed, 100 μg was given in each booster (every six months). Within four weeks, all hens produced excellent antibodies in the eggs. ELISA HS readings averaged 0.95 OD for 1:300 dilution an 0.250 OD for 1:1,200.

EXAMPLE 11

Immunization of Chicken with HSa Immunogen

Selected egg laying hens, White Leghorns, approximately 19 weeks old were injected with the stock HS Immunogen. Four injections (500 μg, 100 μg, 200 μg and 250 μg) were given one week apart. A serum sample was collected two weeks after the last initial injection. If boosters were needed, 100 μg was given in each booster (every six months). Within four weeks, all hens produced excellent antibodies in the eggs. ELISA HSa readings averaged 1.40 OD for 1:300 dilution an 0.576 OD for 1:1,200.

EXAMPLE 12

Preparation of Stock Production Whole Egg Reagents

Selected hens were combined from all four immunogen groups to be used to produce production batches of whole egg reagents. Sterling (U.S. Pat. No. 5,753,228) presents an excellent review of uses for the selection of eggs and storage of the same. The eggs were randomized and shell removed. The whole egg was mixed well and pasteurized using standard conditions (60° C. (140° F.) for 3.5 minutes) Charley, H. and C. Weaver, $3^{rd}$ Edition, Foods: a scientific approach, Merril-Prentice Hall, p. 350, 1998). Once pasteurized, samples were tested for activity and stored at 4° C. until dried or sprayed onto carriers. Samples of 250 μl were analyzed. Examples of results for ELISAs are given:

| Pasteurized Whole Egg: PM, PH, HS, HSa Mixtures | | |
|---|---|---|
| Immunogen | Dilution | O.D. |
| PM | 500 | 0.532 |
| PM | 2500 | 0.113 |
| PH | 500 | 0.466 |
| PH | 2500 | 0.115 |
| HS | 500 | 0.338 |
| HS | 2500 | 0.128 |
| HSa | 500 | 0.588 |
| HSa | 2500 | 0.155 |

EXAMPLE 13

Analysis of Feed Additives for Antibody Activity

Samples of the material were collected from three batches. The samples were analyzed using the ELISA systems for PH, PM, HS and HSa immunogens to monitor activity after pasteurizing and storage. Good antibody response was recorded after the processing of the whole egg batches. Data from three batches from example 20 method of production is given in the table below:

| Batch: Liquid | Pasteurella Immunogen | Signal/Noise | Haemophilus Immunogen | Signal/Noise |
|---|---|---|---|---|
| Batch #1 | 0.347 | 5.32 | 0.111 | 2.68 |
| Batch #2 | 0.188 | 2.92 | 0.175 | 2.93 |
| Batch #3 | 0.272 | 2.98 | 0.138 | 1.91 |

EXAMPLE 14

Testing on Feed Lot Cattle

A group of 222 calves from 2 different sources were shipped to Idaho. 109 calves were processed on day 0 and 113 processed on day 2. All calves received normal vaccination and processing which includes antibiotics designed to reduce disease stress and to increase average daily gain and feed efficiency. Half of the group received the material by intranasal administration. Doses were directly injected into the nostril (1.5 cc/nostril: total 3 ml). The animals were tagged and monitored for 35 days. All calves were housed in the same pen. The Test group had N=111 and the Control group had N=111. The following was observed:

|  | Controls (n = 111) | | Test (n = 111) | |
| --- | --- | --- | --- | --- |
|  | Number | Percent | Number | Percent |
| Pulled to Hospital | 20 | 18 | 7 | 6 |
| Treated for Respiratory Disease | 19 | 17 | 7 | 6 |
| Deaths | 3 | 3 | 0 | 0 |
| Died from Respiratory Disease | 2 | 2 | 0 | 0 |
| Retreats | 5 |  | 3 |  |

EXAMPLE 15

Testing of Feed Lot Cattle

A group of 165 sale barn calves were shipped in the middle of summer Calves were processed on day 0 and on day 2. All calves received normal vaccination and processing which includes antibiotics designed to reduce disease stress and to increase average daily gain and feed efficiency. Half of the group received the material by Intranasal administration. Doses were directly injected into the nostril (1.5 cc/nostril: total 3 ml). The animals were tagged and monitored for 35 days. Test group had N=82 and the Control group had N=83. The following was observed: Controls (n=83) Test (n=82)

|  | Controls (n = 83) | | Test (n = 82) | |
| --- | --- | --- | --- | --- |
|  | Number | Percent | Number | Percent |
| Pulled to Hospital | 36 | 47 | 24 | 28 |
| Treated for Respiratory Disease | 36 | 43 | 22 | 28 |
| Deaths | 9 |  | 5 |  |
| Died from Respiratory Disease | 8 |  | 4 |  |
| Retreat 1X | 14 |  | 12 |  |
| Treated 2X | 10 |  | 4 |  |
| Treated 3X | 4 |  | 3 |  |
| Treated 4X | 3 |  | 2 |  |
| Treated 5X | 6 |  | 1 |  |
| Treatment Cost | $1,291.44 |  | $796.51 |  |
| Ave. Cost per Animal treated | $35.87 |  | $30.64 |  |

EXAMPLE 16

Testing of Feed Lot Cattle

Two groups of calves were shipped to Idaho. 77 calves were processed on day 0 from the first group. Half of the groups were processed as Test (n=39) and other half as Control (n=38). The second group of 78 were processed the same on day 2. All calves received normal vaccination, wormer, implants, and processing which includes antibiotics designed to reduce disease stress and to increase average daily gain and feed efficiency. The Test group received the material by Intranasal administration. Doses were directly injected into the nostril (1.5 cc/nostril: total 3 ml). The animals were tagged and monitored for 35 days. The Test group animals that were pulled to the hospital received booster material along with normal treatment each time they went through the chute. The control cattle received only the normal treatment. The Test group had N=77 and the Control group had N=78. The following was observed:

|  | Controls (n = 78) | | Test (n = 77) | |
| --- | --- | --- | --- | --- |
|  | Number | Percent | Number | Percent |
| Pulled to Hospital | 18 | 23 | 13 | 17 |
| Treated for Respiratory Disease | 18 | 23 | 13 | 17 |
| Deaths | 1 |  | 1 |  |
| Died from Respiratory Disease | 1 |  | 1 |  |
| Retreat 1X | 6 |  | 5 |  |
| Treated 2X | 7 |  | 5 |  |
| Treated 3X | 3 |  | 3 |  |
| Treated 4X | 2 |  | 0 |  |
| RES Realizers | 1 |  | 2 |  |
| RES Deads | 1 |  | 1 |  |
| Death Rate |  | 1.28 |  | 1.30 |
| Treatment Cost | $691.49 |  | $478.59 |  |
| Ave. Cost per Head Pulled | $38.42 |  | $36.81 |  |
| Treatment Cost/Head in Pen | $8.87 |  | $6.22 |  |

EXAMPLE 17

Testing Lick Tubs

The manufacturing process for the lick tubs is very simple and straightforward. The manufacture of this example was done by adding prepared wet material and distillers condensed syrup to standard tubs to adjust the moisture content upward. We substituted dryer material and our liquid material to achieve the same moisture content as standard tubs that are currently being made to achieve a finished tub with similar properties.

The Total Batch Manufactured Lick Tub Example Includes the Following Ingredients:

| | |
| --- | --- |
| Dried Distillers Grains with Solubles (DDGS) | 1170 pounds |
| Corn Gluten Meal | 1365 pounds |
| Wet Distillers Grains | 465 pounds |
| Vitamin and Mineral premix | 750 pounds |
| Mixed Antibody | 540 liters |
| Food grade Molasses | 10 gallons |
| Mold Inhibitor | 6 pounds |

DDGS, corn gluten meal, wet cake, mold inhibitor and premix were placed in a 5-ton mixer truck and mixed for 5 minutes. Then the material and Molasses were added. This was mixed for 30 minutes. The resulting material weighed approximately 5,030 pounds. This mixture was unloaded through a side discharge chute into twenty-eight 200-pound plastic tubs and then compressed into a solid material. The tubs were then cured for 48 hours into a very hard, dark brown product with a somewhat yeasty, sweet odor.

In one trial, one tub was placed near the cattle in a pen of one hundred ninety-seven 600-pound steers. The cattle in the test feedlot were very interested in this material. They visited the tubs several times a day. Consumption was about 7.7 grams/head/day. It is anticipated that per head consumption would have been somewhat higher if more tubs were placed in the pen.

EXAMPLE 18

Development of Top Dressing

One of the key preparations was used for Top Dressing. Specific whole egg was collected from hens immunized with PH, PM, HS and HAs antigens in equal amounts for a total of 7-9 L. The whole egg material was added to 2 L of PBS, pH 7.4, 4.5 L of molasses, and 4 L of distilled water. This was mixed well and preservatives such as food grade vitamin E, vanilla, sodium benzoate, potassium sorbate and sodium citrate were added to prevent microbial growth and extend shelf-life. The total amount is 18 L. The mixture was stirred to get a homogenous solution. The mixture was then pasteurized in a Food Pasteurizer from The Schlueter Company. The material was cooled and stored at 4° C. until used.

This material was poured on top of the feed as needed. It was distributed once every 7 days for a total of three applications.

EXAMPLE 19

Development of Material for Aerosol or Spray

One of the key preparations was used for Aerosol or spray. Specific whole egg was collected from hens immunized with PH, PM, HS and HAs antigens in equal amounts for a total of 10 L. The whole egg material was added to 6 L of PBS, pH 7.4 and 2 L of molasses. This was mixed well and preservatives such as food grade, vanilla, potassium sorbate and sodium citrate were added to prevent microbial growth and extend shelf-life. The total amount was 18 L. The mixture was stirred to get a homogenous solution. The mixture was then pasteurized. The material was cooled and stored at 4° C. until used.

EXAMPLE 20

Animal Testing of Swine

A group of 77 feeder pigs approximately 60 lbs each were tested with material made in Example 18 for Top Dressing. The animals were given the material as a top dressing on days 0, 7, 14 and 21. The average losses on this farm over the last 5 years, due to respiratory complex, was 7.5% and over 30% were medicated during the first 21 days of placement in pens. During the test period of 62 days, all animals were in excellent condition and ahead of schedule with 0% losses and 0% medicated.

EXAMPLE 21

Animal Testing of Swine

A group of 80 feeder pigs approximately 50 lbs were tested with material made in Example 19 for Top Dressing. The animals were given the material as a top dressing on days 0, 7, 14 and 21. The average losses on this farm due to respiratory complex over the last 5 years were 5% during the first 21 days and over 30% were medicated. This was the average for the farm over the last 5 years. During the test period of 55 days, all animals were in very good condition and ahead of schedule and better than in the past with 1.25% losses and 0% medicated.

Any microorganism which colonizes the nasal pharyngeal region of the respiratory tract of its host must possess the capability of sticking or adhering to the surface of the mucus membranes in order to multiply. The respiratory pneumonia complex organisms such as *Pasteurella multocida, M. haemolytica, Haemophilus somnus*, Swine influenza viruses and *Mycoplasma* bacteria are no exception to the rule. Other microorganisms from the fungi and parasite groups are included in organisms that may cause respiratory problems in animals or humans. The adherence inhibitor of this invention strongly interferes with adherence and on a cumulative basis, thereby prevents the specific targeted microorganism from colonizing, and multiplying and moving down the respiratory tract and infecting the lower tract including the lungs. Through the vehicle of a simple nasal injection, spray, by top feed or lick tub, the product essentially supplies the host with specific antibody preparation designed not to cure any disease in the animal but merely to dislodge any resident microorganism and to prevent the attachment of any newly introduced microorganism in the upper respiratory tract. The adherence inhibitor has no direct effect on the host itself, is all natural, leaves absolutely no undesirable residue in the animals, and thus has no effect whatsoever on the ultimate food products. In addition, since the microorganism is prevented from multiplying, it will over time (for example 21-30 days) disappear through natural degradation from mucus of the animal, eliminating the significant potential source of contamination in the feedlot. Properly managed, the risk of cross contaminating other animals throughout the feedlot is lowered and essentially eliminated. Similar applications could be developed for companion animals, zoological animals or nonfood animals or humans. They too have respiratory problems.

EXAMPLE 22

Use of Intranasal Spray in Feedlots

A series of data from seven experiments (two blinded) were conducted and analyzed. Data resulted from studies designed to evaluate an intranasal spray (NP) preparation of avian polyclonal antibodies against various respiratory disease pathogens. The nasal preparation was prepared as described above in Example 20. In most experiments, cattle were procured from at least one sale barn in the southeast US, Texas, Kansas or California. Cattle were processed within 24 h from arrival. In all experiments, cattle received a 4-way MLV on arrival, a 7- or 8-way bacterin (on arrival or 7 to 9 d later), and endectocide (except in the California study). In some of the experiments, cattle received metaphylactic doses of antibiotics. At the time of initial processing and follow-up vaccine booster administration (7 to 9 d), cattle received 3 ml intranasal spray preparation (1.5 ml/nostril). In one of the experiments (Nebraska), an antibody formulation was also offered via a lick tank formula (3 ml/pound). All observations were confirmed and finalized by at least 30 days on feed.

Data were analyzed within each experiment using Chi-square procedures. Results (Table 1) are presented by each study with level of probability for each variable. Where respiratory and non-respiratory data were indicated, they were thus analyzed; otherwise, morbidity and mortality data represent both respiratory and non-respiratory causes.

Feedlot morbidity or mortality was lower in cattle treated with intranasal spray in every study conducted regardless of location, time of the year, sex, in weight, or whether the study was blinded or not (Table 1). In six out of the seven studies, feedlot morbidity was lower (P<0.05) for cattle treated with NP. In the one study where morbidity was not affected (Colorado), mortality was 38% lower (P=0.075) in cattle treated with NP. In one other study (Kentucky, 12/04), there was 88% lower mortality in cattle treated with intranasal spray preparation. Across all experiments (2643 treated vs. 1880 control cattle), treating cattle with NP, once on arrival and 7 to 9 d later, led to lower morbidity (11.7% vs. 26.4%; P=0.00001) and lower mortality (1.2% vs. 3.3%; P=0.00001). Thus, it appears that NP is effective at reducing respiratory disease incidence and resulting death loss when it is a component of an integral health program for receiving feedlot cattle.

TABLE 1

| Study[a] | Blind[b] | Sex[c] | In wt, lb | NP, n | NP, % | Control, n | Control, % | P-value[d] |
|---|---|---|---|---|---|---|---|---|
| KY, 9/04 | NO | H | 438 | | | | | |
| Head received | | | | 63 | | 63 | | |
| Morbidity | | | | | | | | |
| Respiratory | | | | 6 | 9.5 | 29 | 46.0 | 0.00001 |
| Other | | | | 3 | 4.8 | 5 | 7.9 | 0.4650 |
| Responded[e] | | | | 6 | 100.0 | 21 | 72.4 | 0.1430 |
| Mortality | | | | | | | | |
| Respiratory | | | | 0 | 0.0 | 2 | 3.2 | 0.1540 |
| KY, 10/04 | NO | H | 300 | | | | | |
| Head received | | | | 1100 | | 500 | | |
| Morbidity | | | | 66 | 6.0 | 75 | 15.0 | 0.00001 |
| Mortality | | | | 4 | .4 | 3 | .6 | 0.5067 |
| TN, 10/04 | NO | S B | 578 | | | | | |
| Head received | | | | 115 | | 116 | | |
| Morbidity | | | | | | | | |
| Respiratory | | | | 9 | 7.8 | 32 | 27.6 | 0.0001 |
| Other | | | | 2 | 1.7 | 4 | 3.4 | 0.4142 |
| Mortality | | | | | | | | |
| Respiratory | | | | 0 | 0.0 | 2 | 1.7 | 0.1573 |
| NE, 7/04[f] | NO | S | 525 | | | | | |
| Head Received | | | | 88 | | 88 | | |
| Morbidity | | | | 17 | 19.3 | 30 | 34.1 | 0.0268 |
| Mortality | | | | 1 | 1.1 | 8 | 9.1 | 0.0166 |
| KY, 12/04 | NO | S | 640 | | | | | |
| Head received | | | | 135 | | 135 | | |
| Morbidity | | | | 6 | 4.4 | 58 | 43.0 | 0.00001 |
| Mortality | | | | 1 | 0.7 | 8 | 5.9 | 0.0176 |
| CO, 1/05 | YES | S B | 501 | | | | | |
| Head received | | | | 232 | | 233 | | |
| Morbidity | | | | | | | | |
| Respiratory | | | | 136 | 58.6 | 149 | 63.9 | 0.2383 |
| Chronic[g] | | | | 11 | 4.7 | 12 | 5.2 | 0.8389 |
| Mortality | | | | | | | | |
| Respiratory | | | | 19 | 8.2 | 31 | 13.3 | 0.0750 |
| CA, 12/04 | YES | S | 295 | | | | | |
| Head received | | | | 910 | | 745 | | |
| Morbidity | | | | | | | | |
| Respiratory | | | | 70 | 7.7 | 124 | 16.6 | 0.00001 |
| Mortality | | | | | | | | |
| Respiratory | | | | 6 | 0.7 | 8 | 1.1 | 0.3597 |

[a]Study location and date when cattle arrived.
[b]Whether study was blinded or not.
[c]H = heifers; S = steers; B = bulls.
[d]P-value of Chi-square.
[e]To first treatment.
[f]Cattle received follow-up access to a lick tank with NP formula (3 ml/pound).
[g]Number of cattle deemed chronic as a result of respiratory disease.

EXAMPLE 23

Preparation of the Swine Influenza Virus for Immunogen

The swine influenza virus was isolated from herds of swine with endemic influenza episodes. Swabs were taken from varied animals within the herd(s) and transported in viral transport medium to the laboratory for further culture. Each swab culturette fluid was then sterile filtered through a 0.2μ sterile syringe filter (Pall). The filtered supernate was then placed on confluent monolayers of either or both Swine Kidney cells or MDCK (Madin-Darby canine kidney) cells. Initial culture work was in Falcon T-25 sterile cell culture flasks. Cells were grown in Dulbecco High Glucose Medium (DME) with glutamine and 5% calf serum (Hyclone, Inc). All cultures were allowed to incubate at 37° C. in a 4-5% $CO_2$, humidified chamber for a minimum of 7 days. Cultures were examined daily for cytopathology (CPE) typical of influenza virus. Cultures exhibiting signs of contamination or toxicity were discarded.

Cytopathology typical of influenza was detected in 5 of 8 cultures. All culture flasks were frozen at −70° C. to rupture all cells and free virus; this freeze-thaw was repeated 3 times. After the final freeze-thaw, the fluids were aliquoted into sterile 50 ml centrifuge tubes and centrifuged at 2500×G for 10 minutes to spin out cell fragments and debris. The resultant supernate was then aliquoted into sterile storage tubes for testing and identification studies.

Swine Kidney or MDCK cell cultures were prepared in large flasks (Falcon T75 or T225) and grown in DME High Glucose with 5% calf serum. The growth medium was decanted and a 5-10 ml aliquot of the virus fluids was added. This material was allowed to adsorb for a minimum of 30 minutes and no longer than 60 minutes at 37° C., 4% $CO_2$. The virus laden fluids were then removed from the cell layer and fresh DME media without serum was added to each flask.

Cultures were incubated at 37° C., 4% $CO_2$ in a humidied chamber for a minimum of 2 days not to exceed 7 days. All cultures were harvested when they reached at least a 90% CPE. All fluids were pooled into one sterile vessel and frozen at −70° C. until needed for inactivation and immunization. Samples were taken for viral titration. All titration was conducted in swine kidney and/or MDCK or by hemagglutination inhibition testing with turkey, chicken or duck washed red blood cells (Fitzgerald)

Fluids were inactivated by formaldehyde, betapropiolactone (BPL) or binary ethylene amine (BEI) for a minimum of 24 hours. The BEI was the preferred method of inactivation for this virus after studies. It was used for all subsequent work. After 24 hours, the pH was adjusted to 7.2-7.4 and the fluids were adjuvanted with an oil emulsion (MVP Labs).

EXAMPLE 24

Preparation of the Infectious Bovine Rhinotracheitis Virus for Immunogen

The Infectious bovine respiratory virus was isolated from a commercial vaccine. The vaccine was rehydrated with sterile water for injection. Samples for titration were extracted and placed into sterile 15 ml conical tubes (Falcon). The remainder of the vaccine fluids was inactivated with binary ethylene amine (BEI) for a minimum of 8 hours and a maximum of 24 hours. The inactivated fluids were then pH adjusted to 7.2±0.2. The inactivated fluids were then adjuvanted with an oil-water emulsion (MVP Labs).

EXAMPLE 25

Preparation of the Bovine Adenovirus for Immunogen

The bovine adenovirus strains were received from the National Animal Disease Center and the Center for Veterinary Biologics. Each strain was grown on either Vero cells or Madin-Darby Bovine Kidney cells. The frozen cultures received were thawed and added directly to monolayer cultures of either Vero or MDBK cells. The cultures were maintained in DME high glucose medium with 2% calf serum (HyClone Labs). Each culture was maintained for a minimum of 7 days or until cytopathic effect (CPE) typical of an adenovirus infection was observed. Two or more T-75 flasks (Falcon) of each were prepared. When CPE reached 80% or cultures were 7 days old, all cultures were moved into a −70° C. freezer for freezing to release virus from cells. Three freeze-thaws were done with each culture. Following the freeze-thaw, each culture was decanted into sterile 250 milliliter centrifuge tubes and centrifuged at 12,000×g to pellet any cell debris. All supernate fluids were pooled, by strain, sampled for titer and stored in sterile flasks until needed for immunization.

EXAMPLE 26

Analysis of Viral Isolates and Avian Antibodies.

Each of the viral isolates was tested on the appropriate cell substrate in 96 well microtiter plates (Falcon). The swine influenza virus preps were tested on MDCK cells in DME High glucose medium (Hyclone) in 2% calf serum. The virus was titered through 2-fold dilutions up to 10 wells to determine live virus titer. The SIV isolates were also tested by PCR to determine strain and quantity. The strain determinant was an H3N2. Further studies with the SIV for live virus titer and virus neutralization were conducted by hemagglutination and hemagglutination inhibition, respectively, testing in 96 well microtiter plates (conical bottom, CoStar).

The Infectious Bovine Rhinotracheitis virus was tested in 96 well microtiter plates (flat bottom Falcon). The sample was titered on MDBK (Madin Darby Bovine Kidney cells, Center for Veterinary Biologics, Ames, Iowa). The virus was titered through 2-fold dilutions up to 10 wells to determine live virus titer. Dilutions of the virus were also tested by the plaque assay method for both live virus titer and virus neutralization.

Antibodies from Eggs from immunized hens were tested for potency on a weekly basis. The method of testing was dependent upon the immunogen under study. The SIV assay was typically an HAI test for the neutralization of the hemagglutinin of the SIV. Other viruses such as the IBR, BRSV, Bovine adenoviruses and paramyxoviruses were tested for virus neutralization on MDBK cells in either a plaque assay method (IBR) or in a 96 well microtiter plate method.

EXAMPLE 27

Immunization of Chickens with SIV Immunogen

Selected egg laying hens, White Leghorns, 16-19 weeks old were injected with the adjuvanted SIV immunogen. A total of four injections of 1 ml each are given one-two weeks apart. Each injection of 1 milliliter was calculated to contain a minimum of 80 HAI units. Samples from eggs and serum were collected 2 weeks following the last injection. The antibody content was tested by HAI. If antibody levels started to fall, hens were boosted with a 1 ml aliquot at the 80 HAI units.

EXAMPLE 28

Immunization of Chickens with IBR Immunogen

Selected egg laying hens, White leghorns, 16-19 weeks old were injected with the adjuvanted IBR immunogen. A total of four injections of 1 ml each are given one-three weeks apart. Each injection of 1 milliliter was calculated to contain a minimum of $5 \times 10^5$ virus particles per milliliter, pre-inactivation. Serum samples and eggs were collected 2 weeks following the last injection. The antibody content was tested by plaque assay on MDBK cells. If antibody levels started to fall, hens were boosted with 1 ml aliquots of IBR containing at least $5 \times 10^5$ virus particles per milliliter. Repeated studies show that the IBR avian antibodies were consistently generated to titers of 1:32. Studies were conducted to establish the countable number of plaques in a plaque reduction assay format. This was established to be a dilution of $1 \times 10^4$. Replicate studies were done with egg yolk antibodies from different time points, post immunization, to assay for neutralizing antibody titer to IBRV by the plaque reduction method.

The testing resulted in antibody neutralizing responses, when calculated against non-immunized antibody preparations, of 1:8-1:16 using a plaque reduction assay criterion of 80-90% to establish the end point. The USDA standard for passive immunity titers from inactivated vaccines is a 1:2 titer.

It is apparent that many modifications and variations of this invention as hereinbefore set forth may be made without departing from the spirit and scope thereof. The specific embodiments described are given by way of example only and the invention is limited only by the terms of the appended claims. The embodiments of the invention in which an exclusive property or privilege is claimed as follows.

Although the present invention has been described with reference to preferred embodiments, workers skilled in the art will recognize that changes may be made in form and detail without departing from the spirit and scope of the invention.

What is claimed is:

1. An intranasal composition for preventing or decreasing respiratory illness comprising whole egg material and at least a carrier and/or a preservative, the whole egg material comprising egg yolk, albumin and antibody, the whole egg material produced from eggs laid by female birds, wherein the birds are chickens inoculated with one or more viruses or viral antigens causing the respiratory illness, wherein the intranasal composition is formulated for dispersion into the respiratory tract and is effective for preventing and/or reducing the adherence of the virus causing the respiratory illness to the mucosal membranes of the respiratory tract, wherein a dose comprises about 4% by volume of a whole chicken egg, and wherein the carrier and/or a preservative is selected from PBS buffer, molasses, soy oil, DMSO, vanilla, potassium sorbate, sodium citrate and combinations thereof.

2. The composition of claim 1 wherein the composition is formulated for a nasal spray.

3. The composition of claim 1 wherein the antibody in the composition is further formulated for an oral spray.

4. The composition of claim 1 wherein the composition further comprises a mucosal bio-adhesive.

5. The composition of claim 1 wherein the carriers further comprise water, Vitamin E solution and combinations thereof.

6. The composition of claim 1 wherein the composition is further formulated for placement onto an oral strip, wherein the antibody is released when the oral strip is placed in the mouth of the animal.

7. A nasal spray comprising the composition of claim 1.

8. An oral strip comprising an oral formulation of the composition of claim 1.

9. A mouth rinse comprising an oral formulation of the composition of claim 1.

10. The composition of claim 1 wherein the respiratory illness comprises influenza or other viral induced respiratory diseases.

11. The composition of claim 1 wherein the virus or viral antigens comprise $H_1N_1$, $H_5N_1$, $H_3N_2$, Infectious Bovine Rhinotracheitis, 1 and 5, BRSV and $PI_3$, porcine respiratory and reproductive syndrome virus (PRRSv), Bovine adenovirus 1, 3, 5, 6, 7 and combinations thereof.

12. The composition of claim 1 wherein the respiratory illness is in humans.

13. The composition of claim 1 wherein the respiratory illness is in food animals.

14. A method of preventing or reducing the incidence of respiratory illness caused by viruses in an animal, the method comprising:
dispersing an intranasal composition comprising whole egg material, wherein the whole egg material comprises egg yolk, albumin and antibody produced in eggs laid by female birds, wherein the birds are chickens inoculated with one or more viruses or virus antigens causing the respiratory illness, wherein the composition is formulated for dispersion into the respiratory tract and is effective to prevent or reduce the adherence of the virus causing the respiratory illness to the mucosal membranes of the respiratory tract, wherein a dose comprises about 4 percent by volume of a whole chicken egg.

15. The method of claim 14 wherein the composition is further formulated as an oral spray and the dispersing comprises spraying the contents of the oral spray into the mouth of the animal.

16. The method of claim 14 wherein the composition is formulated for oral regimens and placed onto an oral strip and the dispersing comprises placing the oral strip into the mouth of the animal.

17. The method of claim 14 wherein a mouth rinse comprises the composition further formulated for oral regimens and the dispersing is by gargling with the mouth rinse.

18. The method of claim 14 wherein the respiratory illness comprises influenza or other viral induced respiratory diseases.

19. The method of claim 14 wherein the virus or viral antigens comprise $H_1N_1$, $H_5N_1$, $H_3N_2$, Infectious Bovine Rhinotracheitis, 1 and 5, BRSV and $PI_3$, porcine respiratory and reproductive syndrome virus (PRRSv), Bovine adenovirus 1, 3, 5, 6, 7 and combinations thereof.

20. The method of claim 14 wherein the respiratory illness is in humans.

21. The method of claim 14 wherein the respiratory illness is in food animals.

22. The composition of claim 1 further comprising food grade preservatives.

* * * * *